United States Patent [19]

Crilly

[11] Patent Number: 4,941,101

[45] Date of Patent: Jul. 10, 1990

[54] METHOD FOR ANALYZING CHROMATOGRAMS

[75] Inventor: Paul B. Crilly, Coatesville, Pa.

[73] Assignee: Hewlett-Packard Company, Palo Alto, Calif.

[21] Appl. No.: 91,637

[22] Filed: Sep. 1, 1987

[51] Int. Cl.$^5$ .......................................... G01N 31/08
[52] U.S. Cl. .................................. 364/497; 364/498; 364/577; 73/61.1 C; 73/23.23
[58] Field of Search ......................... 73/23.1, 61.1 C; 364/497, 498, 499, 577

[56] References Cited

U.S. PATENT DOCUMENTS

| | | | |
|---|---|---|---|
| 4,180,857 | 12/1979 | Yoshihara et al. | 364/497 |
| 4,215,563 | 8/1980 | Clardy et al. | 73/23.1 |
| 4,266,277 | 5/1981 | Issenmann | 364/498 |
| 4,309,898 | 1/1982 | Horton | 73/23.1 |
| 4,353,242 | 10/1982 | Harris et al. | 73/23.1 |
| 4,357,668 | 11/1982 | Schwartz et al. | 73/23.1 |
| 4,403,503 | 9/1983 | Banerjee et al. | 73/23.1 |
| 4,468,742 | 8/1984 | Jenden et al. | 364/497 |
| 4,546,643 | 10/1985 | Bonneyrat et al. | 73/61.1 C |
| 4,740,903 | 4/1988 | Nakatsuka et al. | 73/23.1 |
| 4,741,198 | 5/1988 | Farren et al. | 73/23.1 |
| 4,752,888 | 6/1988 | Yoshihara | 364/497 |
| 4,802,102 | 1/1989 | Lacey | 364/497 |
| 4,807,148 | 2/1989 | Lacey | 73/61.1 C |

OTHER PUBLICATIONS

P. Jansson ed., Deconvolution with Applications in Spectroscopy pp. 93-134, 1984.
Altmayer, L. H.; "Information from Chromatography Real Time Quantitation"; *Hewlett-Packard Technical Paper No. 89;* Mar., 1979, pp. 1-12.
Anderson, A. H. et al; "Computer Resolution of Unresolved Convoluted Gas-Chromatographic Peaks"; *Advances in Chromatography;* Feb., 1970, pp. 75-83.
Callis, J. B.; "Super Resolution in Chromatography by Numerical Deconvolution"; *Ultrahigh Resolution Chromatography;* Jan., 1983, pp. 171-198.
Crilly, P. B.; "Numerical Deconvolution of Gas Chromatographic Peaks Using Jansson's Method"; *The Pittsburgh Conf. & Exposition, 1987 Abstracts;* Dec., 1986; Abst. No. 554.
Crilly, P. B., "Numerical Deconvolution of Gas Chromatograph Peaks Using Jansson's Method" *Journal of Chemometrics,* vol. 1; Apr., 1987, pp. 79-90.
Crilly, P. B., *"Numerical Deconvolution of Gas Chromatographic Peaks Using Jansson's Method";* Handout accompanying presentation at Pittsburgh Conference; Mar. 1987.
Crilly, P. B.; "Numerical Deconvolution of Overlapped Gas Chromatographic Peaks Using Jansson's Method"; Dissertation submitted to New Mexico State University, May 1987.
Crilly, P. B.; "Evaluation of Jansson's Method for Resolving Overlapped Gas Chromatographic Peaks"; *Journal of Chemometrics,* vol. 1; Jul. 1987, pp. 175-183.
Giddings, J. and Keller, R.; "Extracolumn Contribution to Chromatographic Band Broadening"; *Advances in Chromatography,* vol. 2, 1966, pp. 205-270.
Goldberg, B.; "A Numerical Method of Resolving Peak Areas in Gas Chromatography"; *Journal of Chromatographic Science,* vol. 9; May, 1971, pp. 287-292.
Horlick, G.; "Resolution Enhancement of Line Emission by Deconvolution"; *Applied Spectroscopy,* vol. 26, Nov., 1971, pp. 395-399.
Howard, S., Rayborn, G. H.; "Deconvolution of Gas Chromatographic Data"; *NASA Contractor Report 3229;* 1980, p. i-72.

(List continued on next page.)

Primary Examiner—Parshotam S. Lall
Assistant Examiner—Christopher L. Makay
Attorney, Agent, or Firm—Richard F. Schuette

[57] ABSTRACT

A method for resolving severely overlapped chromatogram peaks using Jansson's iterative deconvolution method is disclosed. The method requires only a knowledge of the impulse response function of the chromatographic apparatus and maximum peak height. A high degree of resolution is achieved without significantly degrading the chromatogram signal to noise ratio.

21 Claims, 5 Drawing Sheets

OTHER PUBLICATIONS

Kirmse, D. W., Westerberg, A. W.; "Resolution Enhancement of Chromatograph Peaks"; *Analytical Chemistry*, vol. 43, Jul., 1971, pp. 1035–1039.

Lacey, R. F.; "Deconvolution of Overlapping Chromatographic Peaks"; *Analytical Chemicstry*; vol. 58, Jun., 1986; pp. 1404–1410.

Mikkelsen, L., Davidson, I.; "Partially Resolved GC Peaks: Analytical Accuracy with an Electronic Integrator"; *Hewlett Packard Technical Paper No. 45*; Mar., 1971, pp. 1–4.

Ramos, L. S., et al; "Third-Order Chromatograph: Multivariate Anal. of Data from Parallel Col. Chrom. with Multichannel Detection"; *Anal. Chem.*, vol. 57; Nov., 1985, pp. 2620–2625.

Rayborn, G. H., et al.; "Resolution of Fused Gas Chromatographic Peaks by Deconvolution"; *American Laboratory*, Oct., 1986, pp. 56–64.

Roberts, S. M.; "Short Cut Fused Peak Resolution Method for Chromatograms"; *Analytical Chemistry*, vol. 44; Mar., 1972, pp. 502–507.

Savitsky A. and Golay, M.; "Smoothing and Differentiation of Data by Simplified Least Square Procedures"; *Analytical Chemistry*, vol. 36, Jul., 1964, pp. 1627–1639.

Schafer, R. W., Mersereau, R. M.; "Iterative Restoration Algorithms"; *Proceedings of the IEEE*, vol. 69; Apr., 1981, pp. 432–450.

Sharaf. M. A. and Kowalski, B. R.; "Quantitative Resolution of Fused Chromatographic Peaks in Gas Chrom.-/Mass Spectrometry"; *Analytical Chemistry*, vol. 54; Jul. 1982, pp. 1291–1296.

Vaidya, R. A., Hester, R. D.; "Deconvolution of Overlapping Chromatographic Peaks Using Constrained Non–Linear Optimization"; *Journal of Chromatography*, vol. 287, 1984, pp. 231–244.

Crilly, P. B.; "Deconvolution of Severely Overlapped Gas Chromatographic Peaks Using a Nonlinear Relaxation"; *FACSS* 14th Annual Meeting, Oct. 4–9, 1987, Detroit, MI.

Harder, A. and de Galan, L.; "Evaluation of a Method for Real-Time Deconvolution"; *Analytical Chemistry*, vol. 46, No. 11, Sep. 1974, pp. 1464–1470.

Roberts, S. M., "Practical Least Squares Approximation of Chromatograms"; *Analytical Chemistry*, vol. 42, No. 8, Jul., 1970; pp. 886–893.

Van Cittert, P. H., *Z Phys.*, 69, pp. 298 (1931).

METHOD FOR ANALYZING CHROMATOGRAMS

BACKGROUND OF THE INVENTION

1. Field of the Invention

This invention is related to a method of analyzing a sample comprised of several components to determine the identity and concentration of each component in the sample. More specifically, this invention is related to a method of analyzing data provided by a chromatographic apparatus to determine the composition of the sample. Even more specifically, this invention is directed to the use of Jansson's method to separate overlapping or "fused" peaks that may be present in the chromatogram provided by the chromatographic apparatus.

2. Description of the Prior Art

Gas chromatography is one of numerous well-known methods of analyzing a sample comprised of several components to qualitatively determine the identity of the sample components as well as quantitatively determine the concentration of those components. A typical gas chromatographic apparatus includes an injection port into which the sample is injected and mixed with an inert gas at high temperature, a column through which the various dissolved components of the sample travel at a rate related to the characteristics of the specific components, and a detector port for measuring the travel or "retention" time of each component in the column. For example, the detector port may comprise means for ionizing the components after they travel through the column and a current detector for detecting photons emitted by the ionizing means. Such a method of measuring component retention time would be used when a flame ionization detector is included as part of the apparatus of the present invention. Alternately, the detector port may comprise means for measuring the gas conductivity of the carrier and sample mixture and means for comparing the measured conductivity to the conductivity of a reference gas (usually a pure sample of the carrier gas). Such a method of measuring component retention time would be used when a thermal conductivity detector is used as part of the apparatus of the present invention in place of the flame ionization detector.

A typical gas chromatogram produced by the above-described apparatus when a flame ionization detector is utilized is a graph indicative of the number of photons detected at the detector port as a function of travel time. When a thermal conductivity detector is utilized instead, the gas chromatogram produced will be a graph indicative of the relative conductivity of photons detected at the detector port as a function of travel time. For both cases, however, as various components will have different column travel times, the gas chromatogram will usually provide a well-defined gaussian-shaped peak for each component in the sample. Since travel time is a unique physical characteristic of each different component, the travel time at which each peak occurs is indicative of the identity of each component in the sample under investigation. Furthermore, peak amplitude or peak area is indicative of the quantity of the specific component in the sample.

Ideally, a gas chromatogram of a sample containing, e.g., two components should have two clearly separate and identifiable peaks. Such a gas chromatogram may be easily analyzed to determine both component identity and quantity by noting the time occurrence and amplitude of each peak. However, in practice, adjacent peaks may be overlapping or "fused" whereby inaccurate determinations of component type and/or quantity result. Fused peaks may be the result of insufficient column length or less than optimum instrument conditions. Fused peaks may also result if the components of the sample are inherently difficult to separate. Processing circuitry following the detector may also degrade peak resolution, thereby contributing to fused peaks. While separation (or "resolution") of fused peaks would permit straightforward analysis of the sample, in many cases, it simply is not possible to completely separate them by prior art techniques.

Early attempts at separating fused peaks consisted of graphical techniques such as tangent skimming, perpendicular drop and shoulder quantitation. Such techniques are discussed in "Partially Resolved GC Peaks: Analytical Accuracy With an Electronic Integrator" by Louis Mikkelsen and Ian Davidson, *Hewlett Packard Technical Paper No. 45*, Avondale Pa., 1971 ("Mikkelsen et al"). Success of the graphical methods described in Mikkelsen et al depends primarily on the ability to detect a shoulder or inflection point in the fused peaks. Such detection may be impossible if the data is noisy or if the peaks are severely fused.

The methods disclosed in Mikkelsen et al are improved by using correction factors. See, "Deconvolution of Overlapping Chromatographic Peaks Using Constrained Non-Linear Optimization" by Rajeev A. Vaidya and Roger D. Hester, *Journal of Chromatography*, vol. 287, pgs. 231–44, Amsterdam, Netherlands, 1984 ("Vaidya et al"). However, even with the correction factor improvements taught in Vaidya et al, these and other graphical methods are still only approximate determinations of the actual chromatograph. Thus, utilization of these methods for separating severely fused peaks produces unsatisfactory results for many applications.

Further improvements in methods for separating fused peaks are achieved using multivariate analysis. Such multivariate analysis of fused gas chromatographic peaks is described in "Third Order Chromatography: Multivariate Analysis of Data From Parallel-Column Chromatography With Multichannel Detection" by L. Scott Ramos et al, *Analytical Chemistry*, vol. 57, pgs. 2620–25, 1985 ("Ramos et al"). However, the method taught by Ramos et al is undesirable since its implementation requires two parallel chromatograph columns coupled to multichannel detectors. Eigenanalysis of the resulting data is said to separate fused peaks. As such a method requires additional chromatographic apparatus, the Ramos et al method proves to be a less than satisfactory method for separating fused gas chromatogram peaks.

Attempts have been made to separate fused peaks by numerical deconvolution. These methods generally involve dividing the Fourier transform of an observed peak by the instrument (i.e., gas chromatographic apparatus) transfer function. See, Resolution Enhancement of Line Emission Spectra by Deconvolution" by Gary Horlick, *Applied Spectroscopy*, vol. 26, pgs. 395–99, 1984 ("Horlick"). Horlick discloses resolution enhancement of gas chromatograph peaks utilizing deconvolution methods whereby the Fourier transform of the observed peak is divided by the instrument transfer function to yield a resolution-enhanced spectrum. Such a method of analysis is unsatisfactory, however, when the signal to noise ratio is poor, since the noise will undesirably figure prominently in the mathematics.

The so-called Wiener filter is common in other deconvolution methods. The Wiener filter provides improved performance over a wider range of signal to noise ratio and provides a better linear estimate of the desired function. The Wiener filter is, however, not well suited for utilization in conjunction with the deconvolution algorithms disclosed by, e.g., Horlick. supra. because use of the Wiener filter often requires prior knowledge of noise and data statistics. These statistics may be difficult to obtain for many of the present applications contemplated for gas chromatograph apparatus.

Another approach is an iterative method of deconvolution. Iterative deconvolution is generally based upon an iteration equation of the form:

$$x_{k+1} = F[x_k]$$

where:
x is the unknown input signal;
F is an operator dependent on the distortion operator which relates the unknown input signal with the known output signal; and
k is the iteration constant.

Such iteration techniques can be useful in gas chromatography if it can be shown that the sequence of approximations $x_k$ converge to one, unique solution.

The ability of an iterative equation to converge to a unique and accurate solution will depend on the impulse response function h(t). "Constrained Iterative Restoration Algorithms" by Ronald W. Schafer et al, *Proceedings of the IEEE*, vol. 69, no. 4, pgs. 432–50, 1981 ("Schafer et al") presents a theoretical discussion of the consequences of error associated with the impulse response function h(t) to the results of iterative deconvolution. Schafer et al further discusses how, under the proper conditions, iterative deconvolution algorithms will converge to a unique solution.

It would appear that an iterative method of deconvolution would provide the best separation of severely fused peaks. However, iterative techniques currently applied to gas chromatograph have been only marginally helpful where severely fused peaks are present.

SUMMARY OF THE INVENTION

It is an object of this invention is to provide a method of separating or "resolving" severely overlapping or "fused" chromatogram peak data to provide information useful in determining the identity and/or concentration of the components of a sample.

Another object of this invention is to provide a method of selectively resolving chromatogram peaks by an amount that depends on the severity of the overlapping.

Yet another object of this invention is to provide a method of analyzing a sample containing two or more components that may have very similar chromatogram characteristics.

Still another object of this invention is to apply Jansson's iterative deconvolution method to chromatographic apparatus data to separate or "resolve" overlapping or fused peaks so that the identity and/or concentration of the individual components in a sample can be accurately determined.

These and other objects are achieved by the present invention of applying Jansson's iterative deconvolution method to separate fused peaks.

According to the invention, a sample containing two or more components is analyzed by a chromatographic apparatus. The chromatogram provided by the apparatus may have overlapping or fused peaks (sometimes also called "unresolvable peaks") of which useful analysis is difficult. The peaks of the chromatogram are separated or "resolved" by the application of Jansson's iterative deconvolution method so that the peaks may be analyzed for composition and quantity. According to the inventive method, the portion of the chromatogram of which analysis is desired is selected. The selected portion is then processed, prior to undergoing peak resolution analysis, to yield a chromatogram function g(t). Next, the impulse response function h(t) is determined for the chromatographic apparatus being used and then appropriately scaled. An iteration variable $k_{final}$ is then selected based on the severity of the overlap or fusing of the peaks of the chromatogram function g(t). A relaxation function r is calculated for the chromatogram function g(t). The chromatogram function g(t) is then deconvolved through $k_{final}$ iterations by applying Jansson's method to yield a true peak shape function x(t) which closely approximates the actual chromatogram for the sample. The true peak shape function x(t) is then analyzed to provide useful information regarding the sample composition and quantity.

BRIEF DESCRIPTION OF THE DRAWINGS

The present invention may be better understood, and its numerous objects and advantages will become apparent to those skilled in the art by reference to the accompanying drawings of which.

DESCRIPTION OF THE PREFERRED EMBODIMENT

A. Theory of the Invention

While the application of the present invention to gas chromatograms produced by gas chromatographic apparatus, it should be clearly understood that the theories and methods described herein are equally applicable to chromatograms produced by other well known analysis techniques such as liquid chromatography.

A chromatographic process can be mathematically modeled by the following equation:

$$g(t) = h(t) * x(t) + n(t) \qquad (1)$$

where:
* is the convolution operator;
g(t) is the gas chromatogram function (i.e. raw data);
h(t) is the impulse response function of the gas chromatographic apparatus;
x(t) is the true peak shape function (which may contain one or more distinct and resolved peaks) of the gas chromatograph; and
n(t) is random noise.

Equation (1) assumes that h(t) is both linear and time invariant over both a specific set of instrument (i.e., gas chromatographic apparatus) conditions and the time period of interest.

The impulse response function h(t) includes peak broadening effects caused by the syringe technique, injection port, column, detector and detector electronics of the instrument and may be modeled as follows:

$$h(t) = h_{syr}(t) * h_{inj}(t) * h_{col}(t) * h_{det}(t) * h_{elec}(t) \quad (2)$$

where:
$h_{syr}(t)$ is the impulse response function of the syringe technique;
$h_{inj}(t)$ is the impulse response function of the injection port;
$h_{col}(t)$ is the impulse response function of the column;
$h_{det}(t)$ is the impulse response function of the detector; and
$h_{elec}(t)$ is the impulse response function of the detector electronics.

If the raw data are sampled, an additional noise term due to quantization must be added to equation (1).

The convolution operator * in equation (1) acts to blur two or more separate peaks contained in the gas chromatogram function x(t). This blurring effect is caused because x(t) loses frequency components when convolved with h(t). If these "lost" frequency components could be recovered, the peaks could then be resolved and the true peak shape x(t) determined.

Figure 1:
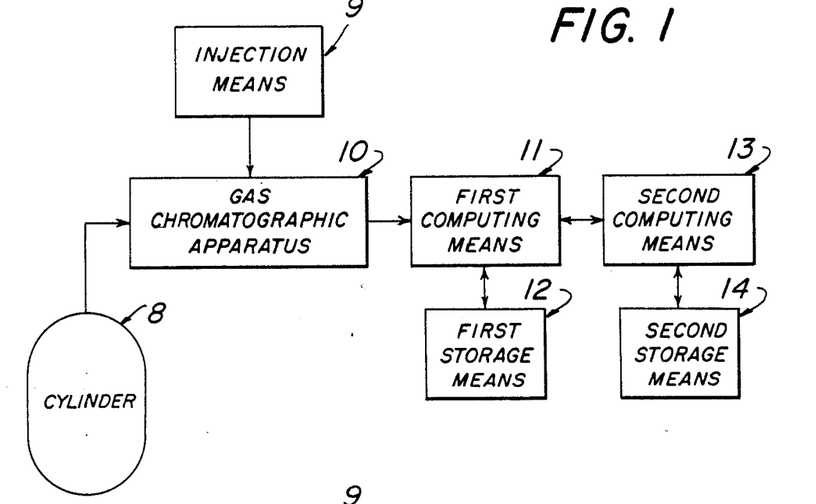
FIG. 1 is a block diagram of an apparatus suitable for practice of the present invention.

If a gas chromatogram derived from the apparatus of FIG. 1 has a single peak (a condition which is indicative of only one component in the analyzed sample), the impulse response function h(t) of the gas chromatograph may be approximated as:

$$g(t) = h(t) \quad (3)$$

This approximation permits the determination of the impulse response function using a sample having one component.

Using Fourier transform techniques, the following expression for a peak shaped gas chromatogram function may be derived:

$$g(t) = F^{-1}[(H(F)) X(F) + N(F)] \quad (4)$$

where:
$F^{-1}$ is the inverse Fourier transform operator;
$H(F)$ is the Fourier transform of h(t);
$X(F)$ is the Fourier transform of x(t); and
$N(F)$ is the Fourier transform of n(t).

Initial attempts to deconvolve the impulse response function h(t) were performed using the equation:

$$\hat{x}(t) = F^{-1}[G(F)/H(F)] \quad (5)$$

where:
$\hat{x}(t)$ is the estimate of x(t); and
$G(F)$ is the Fourier transform of g(t).

Unfortunately, since a gas chromatographic apparatus will have a finite bandwidth, H(F) may have near zero values at some frequencies and G(F) may have finite values due to noise. As can be seen from equation (5), finite values of G(F) and zero values of H(F) results in a "divide by zero" condition; thus the function x(t) "blows up" as the impulse response function h(t) approaches zero. Furthermore, if noise contained in G(F) has negative values, "non-physical" (i.e., not actually existing in the chromatogram) negative peaks may be introduced into deconvolution analysis of the physical data contained in the gas chromatogram.

Another approach to deconvolution is an iterative method where deconvolution is performed according to the equation:

$$\hat{x}^{(k+1)}(t) = \hat{x}^k(t) + b[g(t) - h(t) * \hat{x}^k(t)] \quad (6)$$

where:
$\hat{x}^{(k)}(t)$ is the k'th estimate of x(t);
b is the relaxation constant; and
$\hat{x}^{(0)}(t)$ is g(t) (i.e., the original observed chromatogram (also referred to as the gas chromatogram function)).

Note that equation (6) includes the correction factor:

$$b (g(t) - h(t) * \hat{x}^k(t)) \quad (7)$$

which should be used to adjust the k'th estimate of $\hat{x}(t)$. Upon cursory inspection, this method may provide an improved estimate over that provided by equation (5) since the corrections are done gradually and there are no divisions. However, it can be shown when k is very large, equation (6) will converge to the inverse Fourier transform estimate of x(t) calculated using equation (5).

The estimate $\hat{x}(t)$ will improve, however, if the relaxation constant b is changed to a relaxation function r such that the adjustments will be minor in relatively low signal to noise regions of the peaks. Otherwise, there may be negative correction values if $x^k(t)$ is negative or exceeds a maximum peak value.

Jansson's iterative deconvolution method (hereinafter "Jansson's method") uses this relaxation function r. Jansson's method is discussed in detail in *Deconvolution with Applications in Spectroscopy*, edited by P. Jansson, pgs. 93–134, 1984, appended hereto as Appendix A and incorporated by reference as a part of this specification. Jansson's method may be represented as follows:

$$x^{(k+1)}(t) = x^{(k)}(t) + r[x^{(k)}(t)](g(t) - h(t) * x^{(k)}(t)) \quad (8)$$

with:

$$r[x^{(k)}(t)] = b[(1 - 2/c) |x^{(k)}(t) - c/2|] \quad (9)$$

where:
c is the maximum peak height; and
| | is the absolute value.

The Fourier transform of Equation (8) is:

$$X^{(k+1)}(F) = X^{(k)}(F) + R(X^{(k)}(F)) * (G(F) - H(F) X^{(k)}(F)) \quad (10)$$

The convolution performed by equation (10) will extend the bandwidth of $x^{(k)}(t)$ since R is also a function of X(F). Thus, the convolution operator in equation (10) will blur $X^{(k)}(F)$ in the frequency domain. Increasing the bandwidth results in recovery of the frequency component lost by equation (1). Equations (8) and (9) constrain x(t) to lie within its amplitude bounds, 0 to c.

Function h(t) may be scaled by a constant such that equation (8) becomes:

$$y^{(k+1)}(t) = y^{(k)}(t) + r[y^{(k)}(t)][(g(t) - ah(t) \, y^{(k)}(t)] \quad (11)$$

where a is the scaling constant.

It can be shown that for large values of k that equation (11) will become simply:

$$y^{(k)}(t) = x^{(k)}(t)/a \quad (12)$$

The expression in equation (12) demonstrates that peak height is a function of the h(t) scale factor. Because of the constraint imposed on equation (8) by equation (9), it is important that scale factor a be correctly chosen otherwise equation (8) will not converge.

The convergence of equation (8) will also depend on the selection of relaxation constant b. If the signal to noise ratio of the data is relatively high, b can be large and equation (8) will quickly converge; otherwise b must be a relatively small number or else equation (8) will diverge.

Quantitative analysis of a chromatogram to determine the particular component's concentration requires a peak size measurement. Peak size can be measured by either peak height or area under the peak. Testing has shown for this method that area quantification provides for a more accurate analysis. If good chromatography practice is followed and the capabilities of the instrument are not exceeded then it is reasonable to assume that the system is linear and that peak area measurement will provide an accurate indication of peak size. However, detectors may not respond equally to different compounds. To overcome this distortion, response factors are calculated for the various components detected by the chromatogram and are used to correct a given peak quantity. This is a fairly routine practice that is well known to those skilled in the art and therefore will not be discussed at length.

B. Method of Acquisition and Analysis of Gas Chromatogram Data

Referring first to FIG. 1, an apparatus for acquiring and resolving fused or overlapped gas chromatogram peaks will be described. A sample which may include several components of which analysis is desired is injected by injection means 9, for example a needle-type syringe, into a standard gas chromatographic apparatus 10 to which an inert gas is supplied by cylinder 8. One such gas chromatographic apparatus that may be used in such an application is the Hewlett-Packard model number 5890A. Data from gas chromatographic apparatus 10 is read into a first computing means 11, which may be a Hewlett-Packard HP-85 computer, and stored onto first storage means 12 such as a HP 82901M disc. First computing means 11 processes raw data provided by gas chromatographic apparatus 10 prior to application of the hereinbefore described peak resolution algorithm. First computing means 11 selects the chromatogram data of interest, normalizes the selected data and removes the baseline offset from the selected, normalized data. First computing means 11 thereafter transmits the processed chromatogram data to a second computing means 13. Second computing means 13, which may be a Hewlett Packard HP-9845B computer, processes the received chromatogram data using an iterative deconvolution algorithm based on Jansson's method to yield a high resolution gas chromatogram which includes a distinct peak for each component contained in the analyzed sample. The resolved gas chromatogram is then analyzed by the second computing means to provide useful information regarding sample composition. The processed data, which is also stored in second storage means 14 (for example, a Hewlett Packard HP-9895A disc) is then plotted by any desired means (printer, x-y plotter, etc.) under the control of computing means 13 for display.

Figure 2:
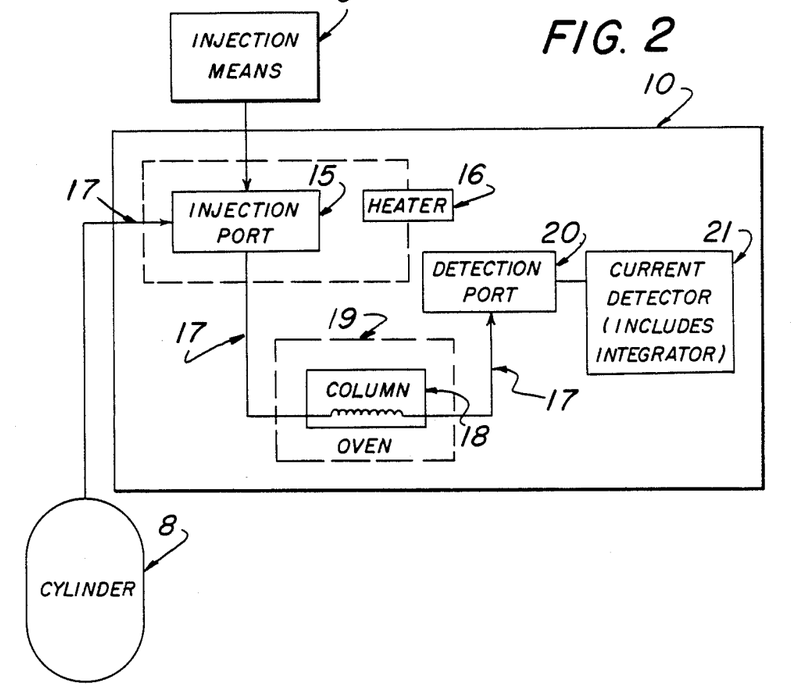
FIG. 2 is a block diagram of a typical gas chromatographic apparatus which may be utilized with the apparatus of FIG. 1.
Figure 4:
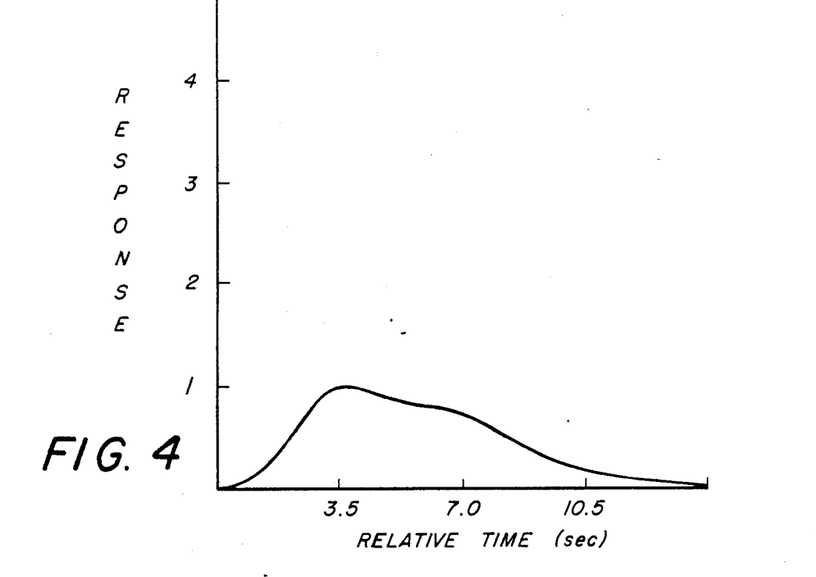
FIG. 4 is a gas chromatogram plot of a sample containing two components acquired by utilizing the apparatus of FIG. 2.

Turning next to FIG. 2, a gas chromatographic apparatus utilized for analyzing a sample will be described. Gas chromatograph apparatus 10 includes an injection port 15, column 18, detector port 20 and current detector 21. An inert carrier gas such as helium flows from cylinder 8 through the lines 17 of gas chromatographic apparatus 10. As the carrier gas flows through injection port 15, heater 16 heats the carrier gas to a desired temperature. A quantity of the sample (which may contain any number of components of which analysis is desired) is injected into injection port 15 by means of a syringe or other injection means 9. The sample evaporates by contacting the hot, inert carrier gas flowing through the injection port 15. The carrier gas, which now carries the evaporated sample, flows along lines 17 and through column 18 to detection port 20. Column 18 is heated and maintained at a desired temperature by oven 19. Chemical affinity between the components dissolved in the carrier gas and column 18 will result in retention of the component by the column 18 for a short period of time. As the chemical affinity between the column 18 and the various components which may make up the sample differs, each component present in the sample will typically have a column retention time different from the other components. Thus, each component of the sample will require a different period of time, known as retention time or column travel time, to pass through column 18 to detection port 20. Detection port 20, which preferably includes a thermal conductivity detector, receives the sample components, senses the presence of each component and converts it into an electrical signal. The thermal conductivity detector consists of two heated wires that feed to a differential amplifier where two resistances are compared. In operation, the thermal conductivity detector injects the components across the first heated wire (or filament) upon their arrival to determine the conductivity of the carrier plus sample. The conductivity of a reference gas (typically a pure sample of the carrier) is determined by injecting the reference gas across the second heated wire (or filament) of the thermal conductivity detector. A comparison of the conductivity of the carrier plus sample as a function of time to the conductivity of the reference gas is performed by the differential amplifier which is provided with the two conductivity determinations and electrical signals corresponding to the conductivity comparisons are outputted by the differential amplifier and used to plot a waveform. The instantaneous characteristics of the waveform produced by the thermal conductivity detector (e.g., amplitude, frequency, etc.) is therefore a function of the comparative conductivity of the carrier plus sample and the reference gas with respect to time. In such a manner, a gas chromatogram is produced that is indicative of the identity of the several components present in the sample. Furthermore, analysis of the gas chromatogram permits the determination of the concentration of those several components present in the sample. For example, the time occurrence of each peak is indicative of component type and peak height is indicative of component concentration or quantity. FIG. 4 shows a typical gas chromatograph which is acquired by using the above-described apparatus to analyze a two component sample. Instrumentation used as well as operating conditions of the apparatus utilized for analysis of a two component sample to produce the gas chromatogram of FIG. 4 are as follows:

| | |
|---|---|
| Gas Chromatograph: | Hewlett-Packard 5890A |
| Integrator: | HP 9845B Desktop Computer |
| Thermal Conductivity Detector | |
| Detector Temperature: | 300 deg. C. |
| Carrier (He) Flow Rate: | 5.2 ml/min |
| Reference (He) Flow Rate: | 5.7 ml/min |
| Split/Splitless Injection Port | |
| Injection Port Temperature: | 200 deg C. |
| Septum Purge: | 2.4 ml/min |
| Split Ratio: | 7:1 |
| Oven Temperature (degrees C.): | 75 |
| Column: | Hewlett-Packard: HP-20M 10X |
| HEWL-12 | 0.53 mm × 1.3 um film |
| Sample 1: | 0.1274 g m-xylene, 0.3323 g ethyl benzene in 5 g of carbon disulfide |

Figure 3A:
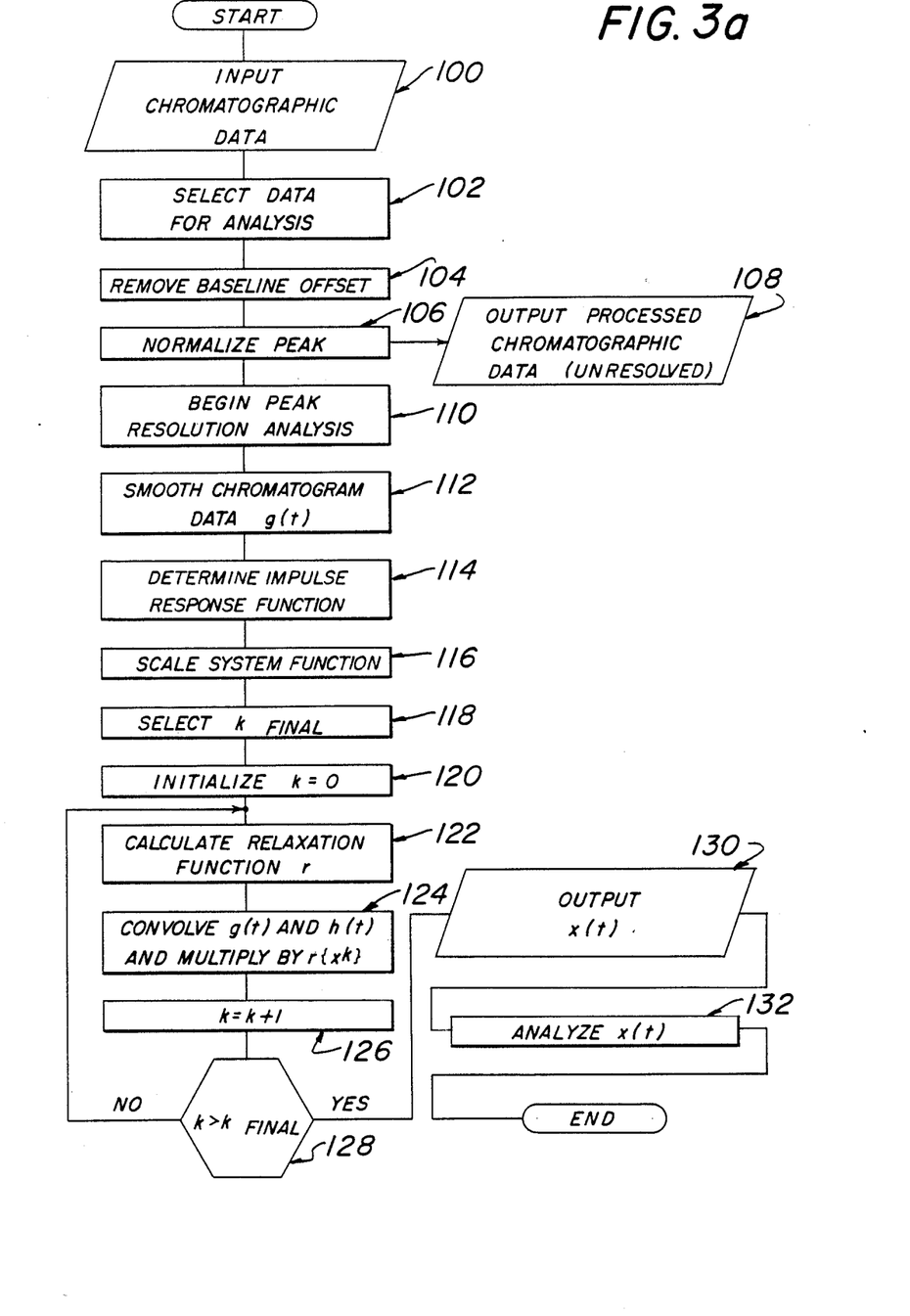
FIG. 3a is a flowchart illustrating the method of the present invention.

Turning next to FIG. 3a, application of the method of the present invention (for analyzing a gas chromatogram produced by the gas chromatographic apparatus 10 of FIG. 2) will be described. The gas chromatogram data is input to first computing means 11 at step 100 for processing of the data. The portion of the gas chromatogram of which further analysis is desired is then selected by the user at step 102. Typically, gas chromatogram data from an analysis of a sample will be produced for several minutes but only a small section of that chromatogram data will provide the useful information necessary to analyze the sample. One method of selecting the useful section of the gas chromatogram data is to determine the maximum peak value of the data, locate the maximum peak value of the data and then strip off all of the chromatogram data not included as part of the chromatogram peak. Once the chromatogram section of interest has been selected and the remainder of the gas chromatogram data removed, the baseline offset of the gas chromatogram is removed at step 104 by shifting the selected data such that it commences at the origin. The gas chromatogram is then normalized at step 106 such that the maximum peak height of the selected chromatogram data has a value of 1. The selected and processed gas chromatogram data g(t) (e.g., FIG. 4) is then output to second computer means 13 for peak resolution analysis as shown at step 108.

Peak resolution analysis of the processed chromatogram data g(t) begins at step 110. The chromatogram data g(t) is first smoothed at step 112 to remove small variations in the processed chromatogram data. Although it is contemplated that any one of numerous well known methods of smoothing may be utilized here, linear interpolation of the processed gas chromatogram data g(t) is the preferred method of smoothing. An impulse response function h(t) for the gas chromatographic apparatus used in producing the gas chromatogram data g(t) is then determined at step 114 according to the method described in steps 114a-f which follow.

Figure 3B:
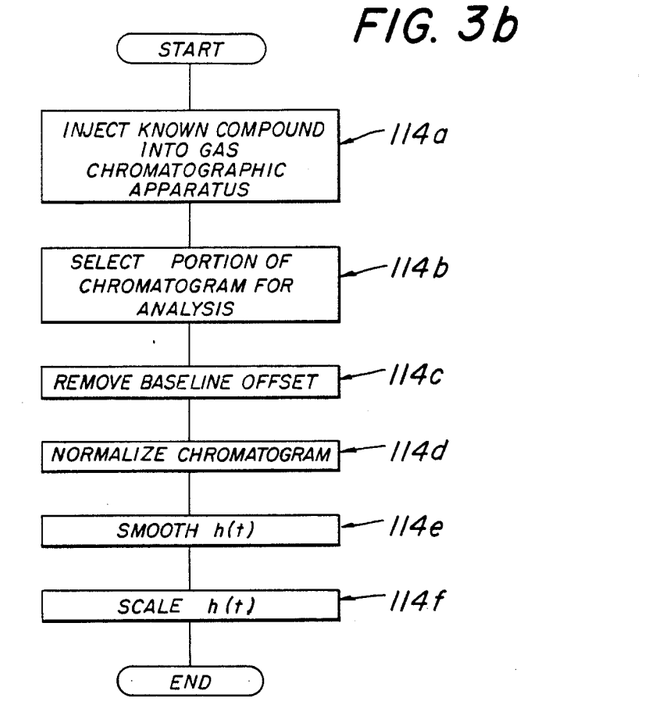
FIG. 3b is a flowchart of the method of determining the impulse response function h(t)
Figure 5:
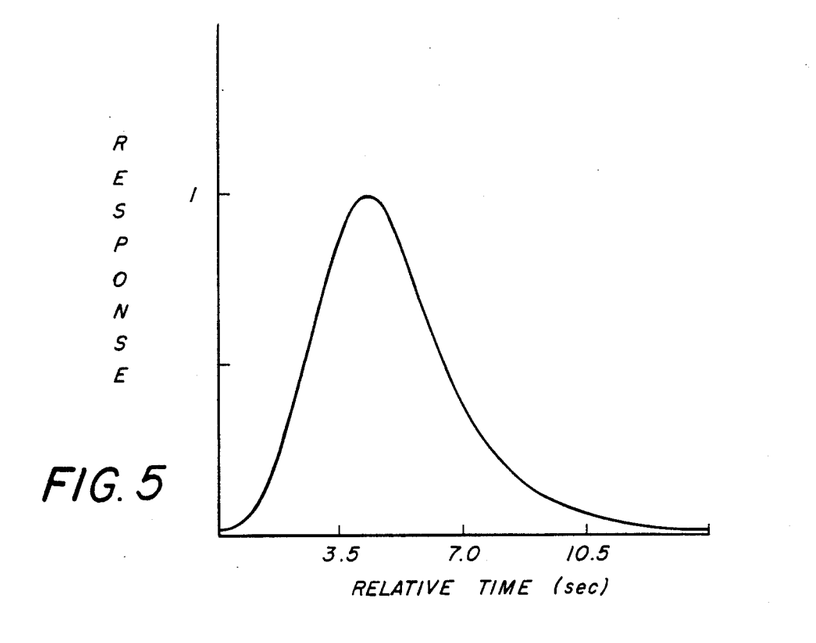
FIG. 5 is the impulse response function h(t) for the gas chromatographic apparatus of FIG. 2.

In general, the impulse response function h(t) is obtained by injection of a pure sample (i.e., one component) whose retention time is known and near that indicated by the fused peak under analysis. In the preferred embodiment of the invention, the impulse response function h(t) is obtained from injection of the gas chromatogram of m-xylene in a solution of carbon disulfide. The resulting impulse response function h(t) is illustrated in FIG. 5. More precisely, the impulse response function h(t) is determined according to the following method. Turning to FIG. 3b, the determination of the impulse response function h(t) commences at step 114a where a single compound of known identity is injected into the gas chromatographic apparatus for analysis. The portion of the gas chromatogram of which further analysis is desired is then selected by the user at step 114b. One method of selecting the useful section of the gas chromatogram data is to determine the maximum peak value of the data, locate the maximum peak value of the data and then strip off all of the chromatogram data not included as part of the chromatogram peak. Once the chromatogram section of interest has been selected and the remainder of the gas chromatogram data removed, the baseline offset of the gas chromatogram is removed at step 114c by shifting the selected data such that it commences at the origin. The gas chromatogram is then normalized at step 114d such that the maximum peak height of the selected chromatogram data has a value of 1. The impulse response function h(t) is then smoothed at step 114e to remove small variations in the processed chromatogram data. Although it is contemplated that any one of numerous well known methods of smoothing may be utilized here, linear interpolation of the processed impulse response function h(t) is the preferred method of smoothing. Proceeding to step 114f, the impulse response function h(t) is initially scaled to the same normalized 0 to 1 scale of the processed gas chromatogram data g(t) as at step 106. The impulse response function h(t) is then rescaled at step 116 so that the total area underneath $\hat{x}(^k\text{final})$ is approximately equal to that of g(t). This scale factor is determined experimentally. If it is not set properly, the method will not converge. Experimental testing has shown that the value of the scale factor a is inversely proportional to the number of sample points z. An iteration constant $k_{final}$ is then selected at 118 for the gas chromatogram data g(t). The value of $k_{final}$ selected depends on the severity of the overlapping of the gas chromatogram data g(t). It has been found that a selection of $k_{final}=40$ has been found to be provide satisfactory results for most gas chromatograms having overlapped peaks. Selecting $k_{final}=80$ should resolve all but the most severely overlapped peaks.

Figure 6:
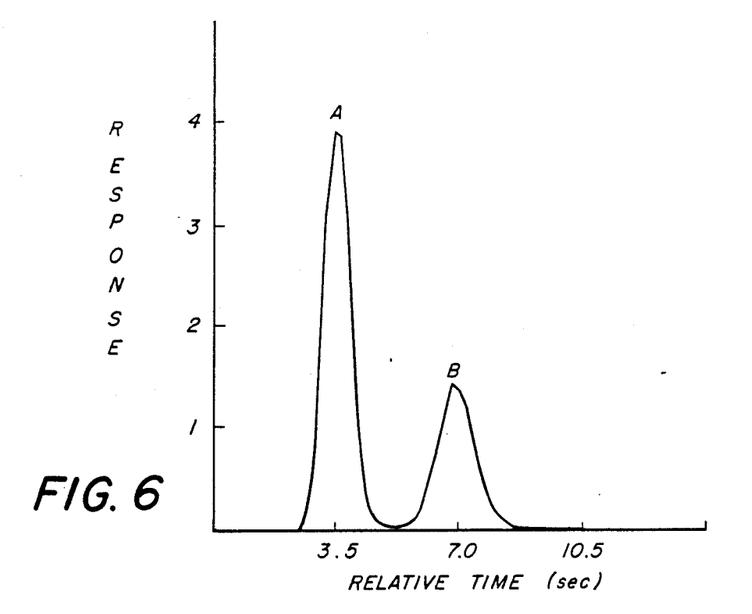
FIG. 6 is a first resolved gas chromatogram plot produced by the method of FIG. 3a for the gas chromatogram plot of FIG. 4.
Figure 7:
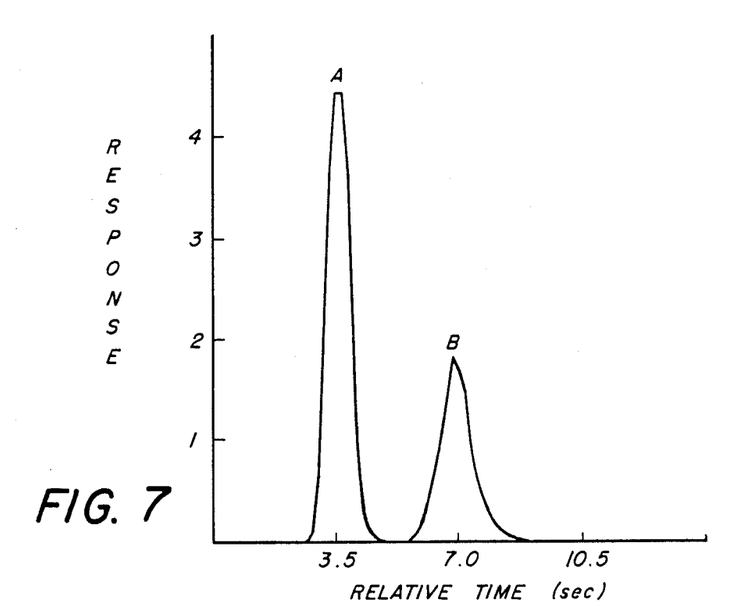
FIG. 7 is a second resolved gas chromatogram plot produced by the method of FIG. 3a for the gas chromatogram of FIG. 4.

Proceeding to step 120, k is initialized at k=0. At step 122, the relaxation function r is calculated for the present value of k according to equation 9. At step 124, the gas chromatogram data g(t) is convolved with the impulse response function h(t) (utilizing the relaxation function r computed in equation (9) according to Jansson's method (equation 8). Jansson's method will yield a function x(t) for the true peak shape. The value of k is then incremented by 1 at step 126. If k is less than or equal to $k_{final}$ at step 128, processing returns to step 122 for further iterations. If k is greater than $k_{final}$, then all iterations have been completed and processing proceeds to step 130 where the estimated true peak shape function x(t) for the analyzed gas chromatogram is output by the second computer means 13 by e.g., a printer or x-y plotter. FIG. 6 shows the gas chromatogram of FIG. 4 after being resolved using the method of the present invention and a value of 40 for $k_{final}$. FIG. 7 shows the gas chromatogram of FIG. 4 after being resolved using the method of the present invention and a value of 80 for $k_{final}$. Returning to FIG. 3a, when step 130 has been completed, the true peak shape function x(t) for the analyzed gas chromatogram is analyzed at step 132 for determination of physical characteristics of the components contained in the sample being analyzed. For example, the time occurrence of each peak may be determined to yield component type and the magnitude of the separated peaks and the area under the separated peaks may be calculated using methods well known in the art to determine component concentration.

There has been described and illustrated a method for analyzing chromatogram data using Jansson's method. However, those skilled in the art will recognize that many modifications and variations in addition to those specifically described may be made in the techniques described herein without departing substantially from the concept of the present invention. Accordingly, it should be clearly understood that the form of the invention described herein is exemplary only, and is not intended as a limitation on the scope of the present invention.

The invention described herein has been embodied in part as a computer program. The listing of a preferred computer program for practice of the invention is included as Appendix B to this disclosure.

What is claimed is:

1. Method of resolving fused peaks present in a chromatogram provided by a chromatographic apparatus, wherein the fused peaks are representative of at least two components of a sample that has been injected into the chromatographic apparatus, comprising the steps of:
   (a) providing a first data set indicative of the chromatogram to the processing means;
   (b) applying, via the processing means, a selected number of iterations of a peak resolution function of the type employing Jansson's iterative deconvolution method to at least a selected portion of the first data set for resolving the fused peaks; and
   wherein the peak resolution function is applied to the first data set according to:

$$x^{(k+1)}(t) = x^{(k)}(t) + r[x^{(k)}(t)](g(t) - h(t) * x^{(k)}t))$$

where:
   $x^{(k)}(t)$ is the k'th estimate of x(t);
   $r[x^{(k)}(t)]$ is the relaxation function;
   g(t) is the first data set;
   h(t) is an impulse response function of the chromatographic apparatus; and,
   (c) providing a second data set representative of the result of the iterations of the peak resolution function; and,
   (d) determining an appropriate retention time for the sample;
   (e) selecting a pure compound having a retention time approximating the retention time of the sample;
   (f) injecting the pure compound into the chromatographic apparatus;
   (g) producing a chromatogram indicative of the impulse response function for the chromatographic apparatus; and
   (h) providing an impulse response function data set indicative of the impulse response function chromatogram to the processing means.

2. Method according to claim 1 further comprising the step of plotting the second data set to provide a graphical representatiave of amplitude versus time.

3. Method of claim 1 wherein the relaxation function is determined according to:

$$r[x^{(k)}(t)] = b[(1 - 2/c) |x^{(k)}(t) - c/2|]$$

where:
b is a relaxation constant; and
c is the maximum peak height of the first data set.

4. Method of resolving fused peaks present in a chromatogram provided by a chromatographic apparatus, wherein the fused peaks are representative of at least two components of a sample that has been injected into the chromatographic apparatus, comprising the steps of:
   (a) providing a first data set indicative of the chromatogram to processing means;
   (b) applying via the processing means, a selected number of iterations of a peak resolution function of the type employing Jansson's iterative deconvolution method to at least a selected portion of the first data set for resolving the fused peaks; and
   (c) providing a second data set representative of the result of the iterations of the peak resolution function;
   (d) analyzing the first data set to determine the severity of fusing peaks of the chromatogram; and
   (e) selecting the number of iterations based on the severity of fusing of peaks of the chromatogram.

5. Method of claim 4 further comprising the step of preparing the first data set prior to applying the peak resolution function to resolve the fused peaks.

6. Method of claim 5 wherein the step of preparing the first data set further comprises the steps of:
   (a) selecting a portion of the first data set for interpretation;
   (b) removing baseline offset from the selected portion; and
   (c) normalizing the selected portion.

7. Method of claim 6 wherein the selecting step further comprises the steps of:
   (a) determining a maximum peak value for the data set;
   (b) locating the maximum peak; and
   (c) stripping off all data from the data set not associated with the maximum peak.

8. Method of claim 6 further comprising the step of scaling the impulse response function with respect to the normalized selected portion.

9. Method of claim 6 further comprising the step of smoothing the selected portion and the impulse response function.

10. Method of resolving fused peaks present in a chromatogram comprising the steps of:
    (a) injecting a sample consisting of at least two components into a gas chromatographic apparatus having an injection port, a column and a detection port;
    (b) analyzing the sample to produce a gas chromatogram;
    (c) providing a first data set indicative of the chromatogram to processing means;
    (d) applying, via the processing means, a selected number of iterations of a peak resolution function of the type employing Jansson's iterative deconvolution method to at least a selected portion of the first data set for resolving the fused peaks; and (e) providing a second data set representative of the result of the iterations of the peak resolution function; and, wherein the step of analyzing the sample to produce a gas chromatogram further comprises the steps of:

(f) evaporating the same with a hot, inert gas;

(g) transporting the evaporated sample from the injection port, through the column, to the detection port; and (h) detecting at least two components of the evaporated sample upon arrival at the detection port; and, wherein the step of transporting the evaporated sample further comprises the step of temporarily retaining each of the at least two components in the column.

11. Method of claim 10 wherein the step of detecting at least two components of the evaporated sample further comprises the steps of:

(a) determining conductivity of the evaporated sample with respect to time;

(b) determining conductivity of said inert gas with respect to time;

(c) determining conductivity differences of said evaporated sample and said inert gas with respect to time; and (d) producing a waveform related to the conductivity difference detected by the detection port as a function of time.

12. Method according to claim 11 further comprising the step of plotting the second data set to provide a graphical representative of amplitude versus time.

13. Method of claim 11 wherein the peak resolution function is applied to the first data set according to:

$$x^{(k+1)}(t) = x^{(k)}(t) + r[x^{(k)}(t)](g(t) - h(t) * x^{(k)}(t))$$

where:
$x^{(k)}(t)$ is the k'th estimate of x(t);
$r[x^{(k)}(t)]$ is the relaxation function;
g(t) is the first data set; and
h(t) is an impulse response function of the gas chromatographic apparatus.

14. Method of claim 13 further comprising the steps of:

(a) determining a retention time for the sample;

(b) selecting a pure compound having a retention time approximating the retention time of the sample;

(c) injecting the pure compound into the gas chromatographic apparatus;

(d) producing a impulse response chromatogram indicative of the impulse response function for the gas chromatographic apparatus; and (e) providing a impulse response function data set indicative of the impulse response chromatogram to the processing means.

15. Method of claim 11 wherein the relaxation function is determined according to:

$$r[x^{(k)}(t)] = b[(1 - 2/c) |x^{(k)}(t) - c/2|]$$

where:
b is a relaxation constant; and
c is the maximum peak height of the first data set.

16. Method of claim 11 further comprising the steps of:

(a) analyzing the first data set to determine the severity of fusing of peaks of the chromatogram; and (b) selecting the number of iterations based on the severity of fusing of peaks of the chromatogram.

17. Method of claim 11 further comprising the step of preparing the first data set prior applying the peak resolution function to resolve the fused peaks.

18. Method of claim 17 wherein the step of preparing the first data set further comprises the steps of:

(a) selecting a portion of the first data set for interpretation;

(b) removing baseline offset from the selected portion; and (c) normalizing the selected portion.

19. Method of claim 18 wherein the selecting step further comprises the steps of:

(a) determining a maximum peak value for the data set;

(b) locating the maximum peak; and (c) stripping off all data from the data set not associated with the maximum peak.

20. Method of claim 18 further comprising the step of scaling the impulse response function with respect to the normalized selected portion.

21. Method of claim 18 further comprising the step of smoothing the selected portion and the impulse response function.

* * * * *